United States Patent [19]

Booth et al.

[11] Patent Number: 5,053,000
[45] Date of Patent: Oct. 1, 1991

[54] OCULAR TREATMENT

[75] Inventors: Christopher G. Booth, Middlesbrough; Raymond C. Rowe, Congleton, both of England

[73] Assignee: Imperial Chemical Industries PLC, London, England

[21] Appl. No.: 514,952

[22] Filed: Apr. 26, 1990

Related U.S. Application Data

[60] Division of Ser. No. 299,689, Jan. 23, 1989, Pat. No. 4,952,212, which is a continuation of Ser. No. 929,476, Nov. 12, 1986, abandoned.

[30] Foreign Application Priority Data

Nov. 13, 1985 [GB] United Kingdom ............... 8528032

[51] Int. Cl.$^5$ ............................................. A61N 1/30
[52] U.S. Cl. ..................................... 604/20; 604/289; 604/294; 604/298; 128/200.14
[58] Field of Search ................... 128/200.14; 604/20, 604/289, 294-296, 298, 300, 301

[56] References Cited

U.S. PATENT DOCUMENTS

| | | | |
|---|---|---|---|
| 2,534,310 | 12/1950 | Silverman | 604/295 |
| 2,698,015 | 12/1954 | Brown | 604/295 |
| 3,934,585 | 1/1976 | Maurice | 604/295 |
| 4,340,047 | 7/1982 | Tapper et al. | 604/20 |
| 4,398,909 | 8/1983 | Portnoff | 604/295 |
| 4,564,016 | 1/1986 | Maurice et al. | 604/20 |
| 4,623,337 | 11/1986 | Maurice | 604/298 |
| 4,758,237 | 7/1988 | Sacks | 604/294 |
| 4,792,334 | 12/1988 | Py | 604/301 |

FOREIGN PATENT DOCUMENTS 1569707 6/1980 United Kingdom.

Primary Examiner—Stephen C. Pellegrino
Assistant Examiner—Michael Rafa
Attorney, Agent, or Firm—Cushman, Darby & Cushman

[57] ABSTRACT

A method of administering less than 20 μl of a solution of an ophthalmically effective substance to the eye characterized in that the formulation has a viscosity and resistivity which makes it suitable for electrodynamic spraying, and the formulation is supplied to a spray nozzle wherein a sufficiently large electrical potential, relative to earth, is applied to the formulation that a sufficient electrical gradient is provided at the spray nozzle to atomize the formulation as a spray of electrically charged droplets. Also liquid solution formulations of opthalmically effective substances for use in the method of the invention; and electrodynamic spraying apparatus, convenient for hand held use, for use in the method of the invention.

9 Claims, 5 Drawing Sheets

OCULAR TREATMENT

This is a division of application Ser. No. 07/299,689, filed Jan. 23, 1989, now U.S. Pat. No. 4,952,212, filed 8/20/90 which is a Rule 60 continuation of application Ser. No. 06/929,476, filed 11/12/86.

The present invention relates to a process of ocular treatment, to formulations useful in such a process and to apparatus suitable for applying such formulations.

A conventional method of ocular administration of a pharmacologically active substance comprises the use of eye drops. This is generally known to have low patient acceptability, especially in the young. The administration of a large drop of liquid to the eye initiates a blink reflex which can cause substantial wastage of an applied active substance by drainage either through the tear ducts or on the skin surface. Indeed it has been reported that if a 30–50 μl drop is applied to the eye the actual volume that reaches the target is 5–7 μl. Therefore, in addition to the low patient acceptability, there is a 4–10 fold wastage. This leads to an inefficiency in the use of expensive ingredients and, in addition, the administrator has little control, and is uncertain, over the amount of ingredient applied to the target.

Another conventional method of ocular administration of an active ingredient comprises the use of an ointment. This similarly has been found to have low patient acceptability and substantial wastage of active ingredient can result.

The present invention provides a solution to these problems of the art by providing accurate dispensing of a low volume of a pharmacologically active substance to the eye. This is achieved by a process which involves electrodynamic spraying of a suitable formulation by raising the formulation to a high potential in a spray nozzle to cause the formulation to atomise as a spray of electrically charged droplets. Such electrically charged droplets seek the closest earthed object to discharge their electric charge, and this can be arranged to be the target area of the eyeball, more particularly the cornea. This process provides a particularly even, accurately targetted, coating of the eye with the formulation.

Figure 1:
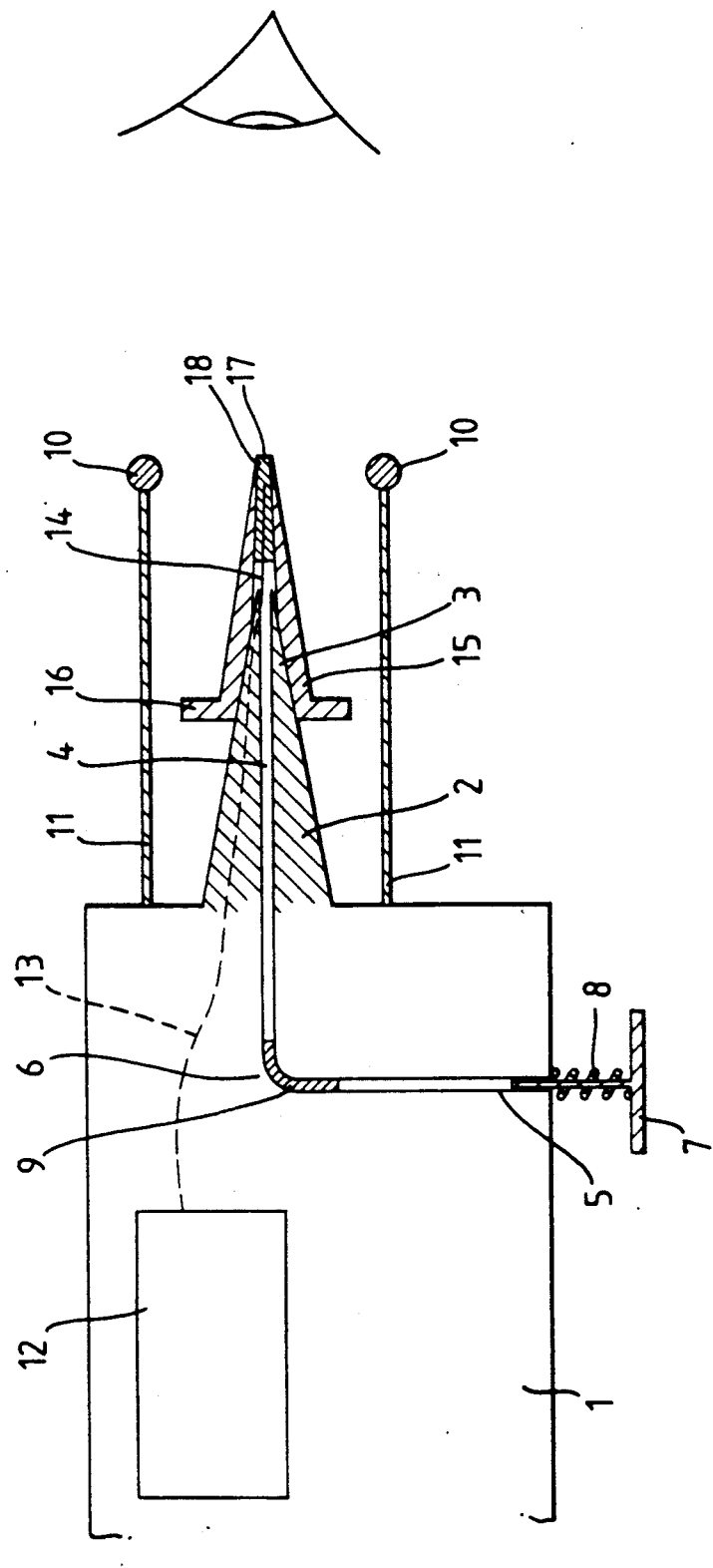
FIG. 1 is a side schematic view of principal components of one embodiment of the apparatus of the invention.

Accordingly, the present invention provides a method of administering to an eye a formulation comprising an ophthalmically active substance and an ophthalmically acceptable diluent, characterised in that the formulation has a viscosity in the range $10^{-3}$ to 1.0 Pa.s (at 25° C.) and a resistivity in the range $10^4$ to $10^{12}$ ohm cm (at 25° C.), and that the formulation is supplied to a spray nozzle wherein a sufficiently large electrical potential, relative to earth, is applied to the formulation from a high voltage generator, that a sufficient electrical gradient is provided at the nozzle to atomise the formulation as a spray of electrically charged droplets.

The method of the invention may be carried out in a unit dose mode, by charging the nozzle with a unit dose from an external source each time it is used, or in a multi-dose mode, in which case a reservoir of the formulation supplies a unit dose automatically to the spray nozzle each time the method is carried out.

In another aspect the present invention provides a liquid solution formulation comprising an ophthalmically active substance and an ophthalmically acceptable diluent which comprises 50% to 100% by weight of an ophthalmically acceptable organic diluent, and from 0% to 50% by weight of water, and has a viscosity in the range $10^{-3}$ to 1.0 Pa.s at 25° C. and a resistivity in the range $10^4$ to $10^{12}$ ohm cm at 25° C.

A suitable such diluent may be a mixture of two or more liquid components.

The ophthalmically active substances encompassed by this invention are any compounds having a pharmacological effect on and/or in the eye. Typical of such compounds are chemotherapeutic agents, compounds to aid ocular examination and compounds to aid surgery; for example (a) anti-inflammatory agents, such as prednisolone and other corticosteroids;

(b) antimicrobial drugs, such as antibiotics, antiseptics, antivirals, fungicides and sulphonamides, for example chloramphenicol, sulphacetamide, gentamycin, nystatin, acyclovir and idoxuridine;

(c) autonomic drugs, such as β-adrenoceptor antagonists, cycloplegics, miotics, mydriatics and vasoconstrictors, for example timolol, atenolol, pilocarpine, atropine, tropicamide, hyoscine, ephedrine, phenylephrine, carbachol, guanethidine and adrenaline;

(d) local anaesthetics, such as lignocaine or oxybuprocaine;

(e) diagnostics, such as fluorescein;

(f) drugs to assist healing of corneal abrasions, such as urogastrone and epidermal growth factor (EGF);

(g) drugs of use in diabetic retinopathy, such as aldose reductase inhibitors, for example sorbinil and 3-(4-bromo-2-fluorobenzyl)-4-oxo-3H-phthalazin-1-ylacetic acid;

of which (c) is the most important group, and (f) and (g) are also particularly important.

As hereinbefore discussed, conventional methods of ocular administration lead to wastage of ingredient for example by drainage through the naso-lachrymal duct into the throat, and subsequent ingestion into the gastro-intestinal tract, whence it can be absorbed systemically, and exert undesired side-effects. For example, it is well documented in the literature that β-adrenoceptor antagonists administered as eye-drops can exert a significant cardiovascular effect, as a result of such ingestion into the gastro-intestinal tract.

The present invention enables accurate targetting of a fine spray of electrically charged particles of the formulation to dose the required amount, thereby substantially eliminating unwanted side-effects.

The formulation may not be predominantly aqueous as it has been found that aqueous formulations do not undergo electrodynamic spraying satisfactorily due to their high conductivity. Preferably, the amount of water, if any is present, comprises not more than about 20% by weight of the total diluent, and preferably less than 10% by weight.

Certain diluents have viscosity and resistivity properties such that they may be used alone as the sole solvent component in the formulation. Such solvents are, for example, dimethylisosorbide, glycerol, propylene glycol, polyethylene glycol of average molecular weight up to about 600, maize oil and arachis oil.

Certain other solvents or diluents are appropriate for use in the formulation as one of two or more diluent components. Formulations containing high proportions, more than 50%, of water, are as previously stated, generally unsuitable for electrodynamic spraying due to their high conductivity. Some solvents, for example surfactants such as polyethoxyethylated castor oils ("Cremophors"), polyoxyethylene-polyoxypropylene block copolymers ("Pluronics", "Synperonics"), polyoxyethylene sorbitan derivatives ("Tweens"), polyoxyethylene oleyl ethers ("Brijs"), castor oil and olive oil, may be irritant to the eye when used alone, but can be used satisfactorily in admixture with, for example, dimethylisosorbide, to give a formulation of suitable resistivity.

Viscosity can be adjusted to within the required range by the addition of viscolysers, for example hydroxypropylcellulose, hydroxypropylmethylcellulose, methylcellulose, polyvinyl alcohol or polyvinylpyrrolidone.

The formulation also preferably contains a preservative, such as benzalkonium chloride, benzyl alcohol, chlorbutol, disodium edetate, p-hydroxybenzoates or thiomersal, since certain of the diluents used are good substrates for bacterial growth.

In order to bring the resistivity of the formulation into the range $10^4$ to $10^{12}$ ohm cm, if necessary, a resistivity modifier may be present. This is generally a charged species such as a salt, for example sodium chloride or a salt conventionally used in pharmacologically acceptable buffers, for example sodium acetate, disodium hydrogen phosphate or sodium dihydrogen phosphate. When the major diluent is not itself a surfactant, the formulation may optionally contain a small amount of one of the above-mentioned surfactants to aid the flow characteristics.

Specific diluents and solvent systems which are sprayable from the apparatus of the invention are as follows:

| Diluent | Viscosity PaS | Resistivity ohm cm |
| --- | --- | --- |
| Glycerol | .950 | $3.4 \times 10^7$ |
| Propylene glycol | .045 | $2.7 \times 10^7$ |
| Polyethylene glycol 400 | .090 | $1.8 \times 10^6$ |
| Dimethyl isosorbide | .008 | $6.4 \times 10^8$ |
| Maize oil | .063 | $7.5 \times 10^{10}$ |
| Glycerol:water (9:1) | .197 | $2.2 \times 10^6$ |
| Dimethylisosorbide:water (9:1) | .008 | $4.1 \times 10^6$ |
| Dimethylisosorbide:glycerol:water (4.5:4.5:1) | .064 | $6.4 \times 10^6$ |
| Dimethylisosorbide:water (9:1) + 4% w/w hydroxypropyl cellulose | .528 | $5.3 \times 10^5$ |
| Dimethylisosorbide:Synperonic NP8 (9:1) | .010 | $1.1 \times 10^7$ |
| Dimethylisosorbide:Tween 80 (9:1) | .011 | $4.0 \times 10^7$ |
| Dimethylisosorbide:Maize oil (9:1) | .018 | $2.5 \times 10^8$ |

* Viscosity was measured with a Rotovisco model RV12 - Haake Mess-Technik GmbH, West Germany.
* Resistivity was measured with a Solid State Electrometer model 602 Kiethley Instruments, Cleveland, Ohio.

Suitably the active ingredient is in the formulation in a concentration range of 0.1 to 20%, and preferably 5 to 10%, but the required concentration depends, naturally, upon the potency of the particular drug being used.

The formulation is generally provided as a liquid for direct use, but it is possible that it is constituted shortly before use. Thus in another aspect the present invention provides two-part package comprising active ingredient in the first part, generally as a concentrated solution, and a suitable diluent or co-solvent in the second part. In use, the two parts are fed into a mixing chamber in the spraying apparatus, before being fed to the nozzle or spray head.

British specification 1569707 discloses an electrostatic spraying apparatus which comprises a spray nozzle charged to a potential of 1-20 KV from a high voltage generator, a reservoir for supplying liquid to the nozzle and an earthed field intensifying electrode disposed around the nozzle. The high potential produced between the spray nozzle and the electrode is sufficient to draw the liquid away from the nozzle towards the electrode as one or more ligaments of electrically charged liquid. At a certain distance from the nozzle surface the ligament or ligaments break up to form a divergent spray of electrically charged droplets. The ligament length depends on the applied field strength and the characteristics of the liquid.

The apparatus described in the above mentioned specification includes hand-held devices as well as tractor and aircraft mounted devices. The apparatus is described as being readily used for many purposes wherein atomisation and deposition, or atomisation alone, are required.

In a preferred aspect of the present invention apparatus is provided that sprays a metered dose of low volume for example 20 μl or below, more suitably 10 μl or below and preferably about 5 μl.

Accordingly the present invention provides electrodynamic spraying apparatus for dispensing a liquid solution formulation as claimed in claim 1, which comprises:

(i) at least one spray nozzle having an outlet of sufficiently small cross section to be capable of retaining therein up to 20 μl of the formulation by surface tension;

(ii) means to supply a measured volume of up to 20 μl of the formulation to said nozzle; and (iii) means for applying a potential difference between said spray nozzle and an electrode spaced from said spray nozzle;

so that an electrical field of sufficient strength is provided at the outlet of the spray nozzle to draw the formulation away from said outlet as one or more ligaments.

To obtain a ligament forming field a large potential difference has to be established between the dispensing member element and the electrode. For simplicity and ease of description it will be assumed that the electrode is at earth potential and references hereinafter to "earth" refer to the potential of the electrode and a voltage refers to a potential relative to that of the electrode. It will be appreciated that the electrode need not in fact be at a positive or negative potential relative to true earth. The voltage at the dispensing member may be negative or, preferably, positive relative to the electrode.

Conveniently the electrode is a field intensifying electrode. Field intensifying electrodes and their use are described in British Specification 1569707. As stated therein the field intensifying electrode acts as a 'dummy' target and, as it can be in a fixed position relative to the position or positions from which ligaments of liquid are capable of being formed, the field around the ligament forming positions is constant for a given voltage giving rise to results of greater uniformity. Furthermore as the 'dummy' target is nearer the dispensing member element than the article being sprayed a higher field strength is created than would otherwise be the case, enabling a lower voltage to be used. This obviates the need for generating voltages of the order of 60–100 KV as in other forms of electrostatic spraying.

The field intensifying electrode is generally situated as close as possible to the position or positions from which ligaments are formed on the dispensing member element. Either one field intensifying electrode or a plurality of field intensifying electrodes can be provided depending on the configuration of the dispensing member and where it is desired to create the electrical field of sufficient magnitude to form the ligaments.

The, or each, field intensifying electrode is suitably positioned in front of, or level with, the part of the dispensing member element from which ligament formation occurs. The, or each, field intensifying electrode is optionally sheathed with an insulating material, thereby allowing the electrode to be positioned nearer to the spray nozzle resulting in a stronger field effect in the region of the dispensing member element. Optionally the, or each, field intensifying electrode is adjustably mounted to enable a variation of distance between said electrode and the dispensing member element thereby altering the spray characteristics as desired.

Suitably the apparatus is provided with a metered valve or a syringe-pump, such as those used for multi-dose administration of insulin, to control the passage of the liquid formulation from a reservoir to the spray nozzle. In an alternative aspect accurately measured low volumes can be supplied to the apparatus by placing the spray nozzle in the liquid formulation and drawing in the required amount by means of pipette action, for example using a piston in a syringe. Pipette action can also be used to urge the formulation from the apparatus when in use.

In a preferred aspect of this invention we have found that the best spraying results are achieved using a modification of previous apparatus wherein the spray nozzle is demountable from the apparatus. In use the required dose of formulation is supplied in a spray nozzle which is then located on the spraying apparatus in any convenient manner such as by screwing or by friction-fit on an appropriate receiving member. In this way the low volume of formulation is conveniently measured, in any conventional manner, prior to use.

Suitably the apparatus is provided with means to keep the flow rate sufficiently low so that atomisation of the small volume of formulation has time to take effect. The means for supplying the formulation to be sprayed to be nozzle tip will generally comprise a piston which, in use, will drive a column of air through a tube to the nozzle thus causing the formulation therein to flow, and as a potential is applied, to atomise. Optionally in such an arrangement there is damping means in the tube to aid control of the flow rate of the column of air, for example a viscous liquid slug.

In an alternative the flow rate of the air column can be controlled by means of a metered pump or valve. Conveniently the means for supplying liquid to the spray nozzle tip, for example a metered pump or valve or a piston, is manually or electrically operated by a push-button or trigger which simultaneously activates the high voltage generator that supplies high voltage to atomise the formulation. A suitable metered pump is one of the type used for administering successive doses of insulin from a multi-dose device, as supplied by Muirhead Vactric Components Ltd. of Beckenham, Ky.

Generally the apparatus useful in this invention is hand-held and comprises one or two spray nozzles depending on whether it is desired to treat eyes separately or concurrently. Conveniently the high voltage required to effect atomisation of the formulation is provided by a battery-powered high voltage generator contained in hand held apparatus. In another convenient aspect the voltage may be provided by a piezoelectric generator. The battery or batteries for such a generator is/are also conveniently located in the apparatus which is suitably dimensioned for hand-held usage. In an alternative the high voltage can be generated in a remote pack and supplied by high tension lines to a hand-held spraying apparatus.

The nozzle configuration is determined by the requirement that the formulation does not flow or drip therefrom in the absence of an applied high potential and in the absence of a contacting surface. The configuration is not critical and may, for example, have edges defining an orifice of rectangular, elliptical or circular cross-section.

The nozzle configuration can affect the volumetric flow of liquid through, and from, said nozzle as the potential is applied and hence the volumetric spraying rate. As previously mentioned the nozzle may be mountable and demountable from the spraying apparatus so that the flow rate can be varied by using nozzles of various configurations.

Suitably the electrical field of sufficient strength to atomise the formulation as a spray is provided by a means for electrically charging the spray nozzle to a potential of the order of 1–20 kV and having a field adjusting electrode, at earth potential, mounted adjacent to the spray nozzle. Field adjusting electrodes are described in U.S. Pat. No. 4,476,515. The field adjusting electrode can be separated from the nozzle by means of an air-gap, for example of about 2 cm, or preferably by means of an insulating material. If the field adjusting electrode is adjustably mounted then the distance between said electrode and the nozzle can be varied thus affecting the electrical field on the liquid and altering the spray droplet size and angle of spray.

An embodiment of the invention in unit dose form is now described, by way of example only, with reference to the accompanying drawing, FIG. 1, which is a schematic view illustrating the principal components of one form of the apparatus.

Referring to FIG. 1 there is a body member 1 sized so as to be capable of being hand held. On one wall of the body member 1 there is mounted a conical receiving member 2 that tapers to an end 3. Centrally positioned in the end 3 of the member 2 is the outlet of a tube 4, circular in cross-section, that extends centrally through the conical member 2, through the body member 1 and has an inlet 5 in another wall of said member 1. The tube 4 is of substantially uniform cross-section and has a 90°. bend therein at region 6. At the tube inlet 5 there is a piston 7 sized so as to form a friction fit. The piston 7 operates against a spring 8. In the tube 5, at the region 6, there is provided damping means 9 in the form of a viscous liquid slug.

Disposed about 2 cm distance from the end 3 of the conical member 2 is a field adjusting electrode in the form of a ring 10. This ring 10 is spaced from the body member 1 by means of a cylindrical collar 11.

The body member 1 contains therein a battery powered high voltage generator 12 that is connected by electrical switching means (not shown) to the piston 7. From the generator 12 extends a lead 13 that is embedded in the conical receiving member 2 and exits therefrom in the region of the end 3, to provide a protruding portion 14.

In addition there is provided a demountable hollow spray nozzle 15 of generally conical shape. The nozzle 15 is sufficiently resilient to be able to form a friction-fit on to the extended surface of the conical receiving member 2. To facilitate the urging of the nozzle 15 on to the member 2 an annular flange 16 is provided on said nozzle. The hollow centre of the nozzle is of conical configuration and there is a small aperture 17 at the tip of said nozzle. The aperture 17 is sufficiently sized so that formulation is held within the nozzle by surface tension and other effects.

A metered dose of a formulation 18 is provided within the demountable nozzle 15.

In use the piston 7 is depressed against the spring 8. This causes a current of air to move through the tube 4, the slug 9 acting as a damping control on the passage of air. The current of air passes into the hollow spray nozzle 15 and urges the formulation 18 through the aperture 17 of the tip of said nozzle in the direction of a target eye. At the same time the piston 7 activates the high voltage generator (by means not shown) which in turn causes a high voltage of the order of 16 kV to pass through lead 13 which in portion 14 thereof is in contact with the formulation 18. Thus the formulation 18 is raised to a high potential. The ring field adjusting electrode 10 is at earth potential. Thus as a result of the urging of the current of air and the high potential difference the formulation is atomised as a spray of electrically charged droplets to give a particularly even targetted coating of the target eye.

Figure 2:
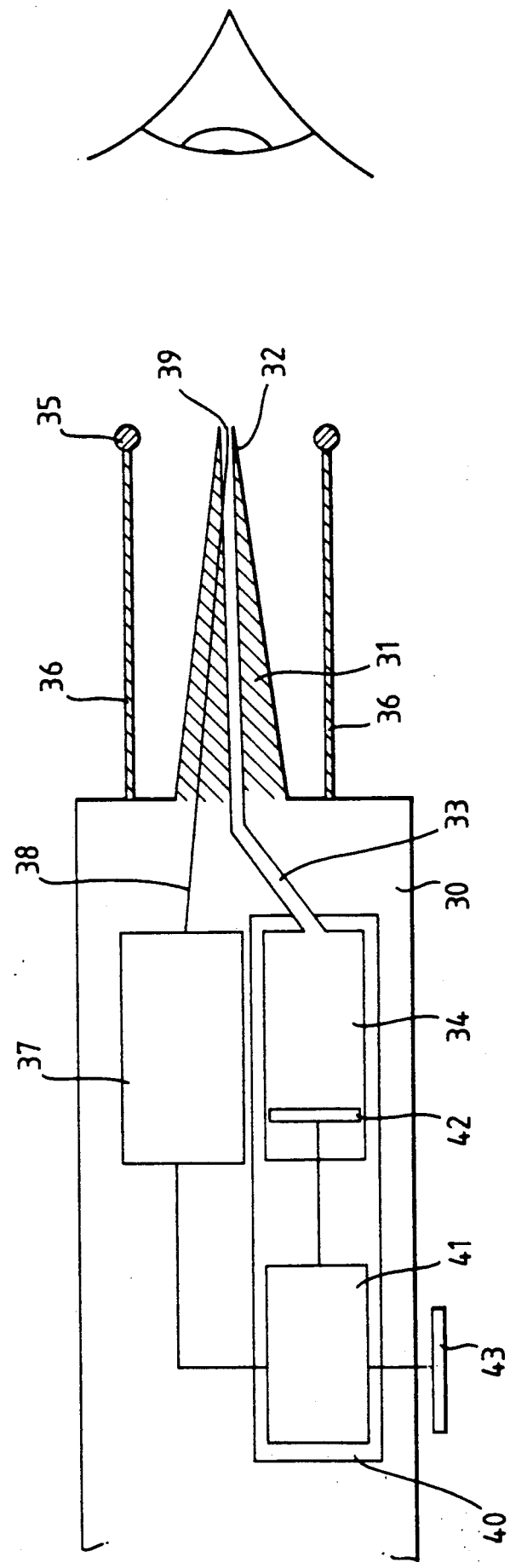
FIG. 2 is a side schematic view of the principal components of a multi-dose embodiment of the apparatus of the invention.

An alternative embodiment of the invention, in multi-dose form, will now be described, by way of example only with reference to FIG. 2 of the accompanying drawings, which is a schematic view of the principal components of this multi-dose form of the apparatus.

As in the unit-dose form of apparatus described above there is a body member 30 sized so as to be capable of being hand held. On one wall of the body member 30 there is mounted a conical nozzle 31 that tapers to an end 32. Centrally positioned in the end 32 of the nozzle 31 is the outlet of a tube 33, of uniform, circular cross section, that extends centrally through the conical nozzle 31 to a syringe, 34 forming part of a syringe pump 40 accommodated within the body member 30. Disposed about 2 cm. distant from the end 32 of the conical nozzle 31 is a field adjusting electrode in the form of a ring 35, spaced from the body member 30 by a cylindrical collar 36. The body member 30 additionally accommodates a battery powered high voltage generator 37, from which extends a lead 38 that is embedded in the conical nozzle 31, and exits therefrom into the tube 33 near its end 32 to provide a protruding portion 39.

Alternatively, the lead 38 can be adapted to make contact with the liquid being dispensed at any point of the syringe 34 or the tube 33.

The syringe-pump 40, of the type supplied by Muirhead Vactric Components Ltd. of Beckenham, Kent, for administering successive doses of insulin from a reservoir syringe, comprises a mini-pump 41 which drives the plunger 42 of a replaceable syringe 34, to dispense an accurately metered amount of the syringe contents through the outlet 32 of the conical nozzle 31 whenever the syringe pump 40 is activated, by activating means, shown here as a press button, 43.

In use, the syringe 34 contains a formulation of an ophthalmically active substance according to the invention. Operation of the activating means 43 causes an accurately metered quantity of the formulation, of the order of 5 $\mu$l, to pass out through the end 32 of the conical nozzle 31. At the same time, the operation of the actuating means 43 switches on the high voltage generator 37 to supply a high voltage via the lead 38 to the protruding portion thereof 39, thus applying a high electrical potential to the formulation being discharged from the end 39 of the conical nozzle 31.

EXAMPLE 1

Ephedrine (350 $\mu$g) was formulated as a 10% solution (3.5 $\mu$l) in a mixture of dimethyl isosorbide: water (9:1) which also contained hydroxypropyl cellulose (4% wt/wt).

This formulation was sprayed, from the apparatus described hereinbefore in the specific embodiment, on to one eye of each of six male New Zealand white rabbits. The other eye remained untreated to act as a control allowing compensation for changing environmental factors to be included in the calculation of the results.

Figure 3:
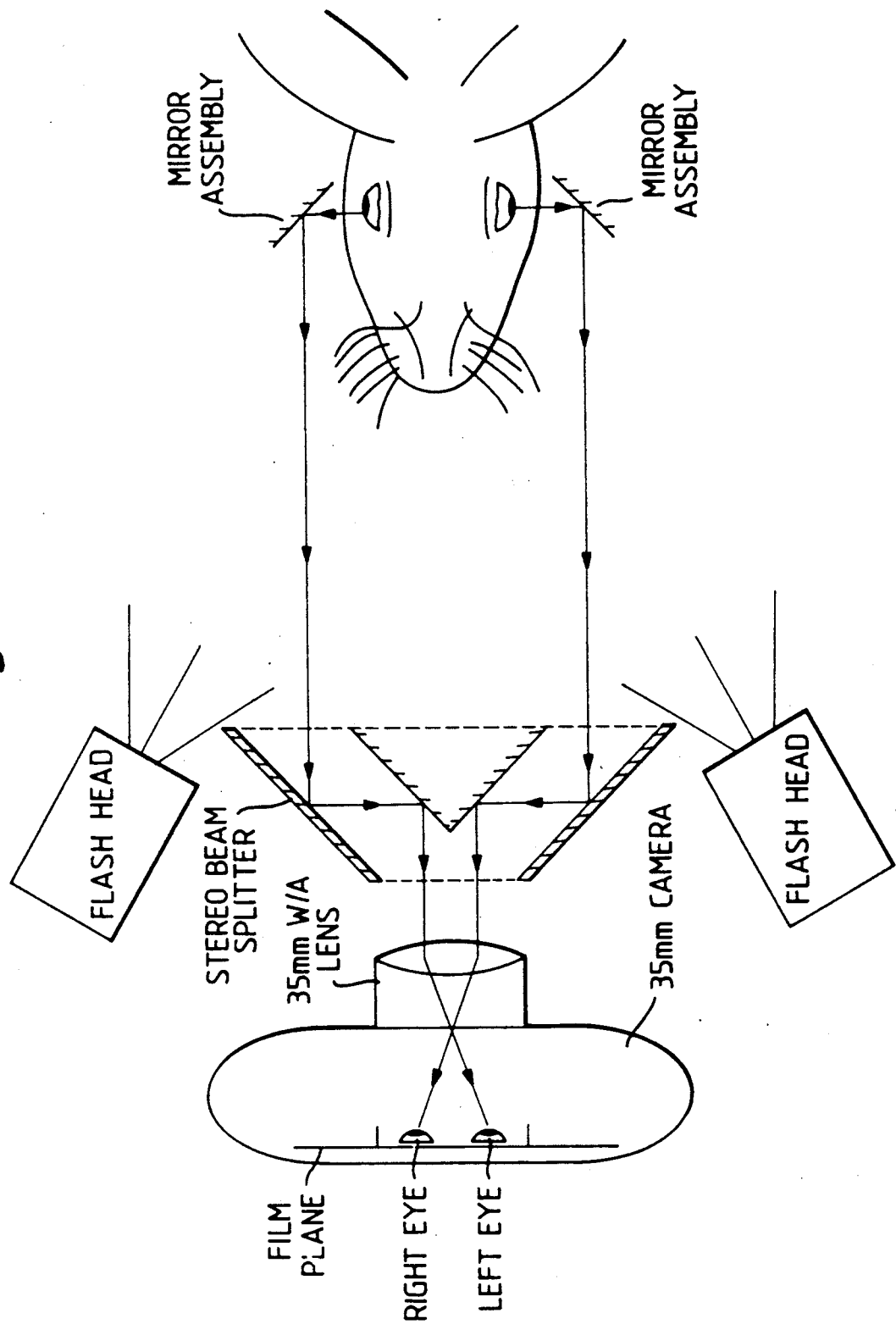
FIG. 3 shows a top view of a camera and optical system suitable for use in recording mydriasis resulting from the topical application of the formulation of the invention to the eye.

Mydriasis resulting from the topical application of the formulation to the eye was recorded on photographic film using a camera and optical system as depicted in FIG. 3. The pupil diameters were measured from the projected images of the processed film using engineer's calipers.

The mydriatic response of the treated eye to ephedrine was calculated as follows:

$$\frac{T_t - T_o}{T_o} - \frac{C_t - C_o}{C_o} \times 100 =$$

% increase in pupil diameter at time ($t$).

where: $T_o$ and $C_o$ are the pretreatment pupil diameters of the test and control eyes respectively, and $T_t$ and $C_t$ are the pupil diameters of the test and control eyes respectively at time(t).

Figure 4:
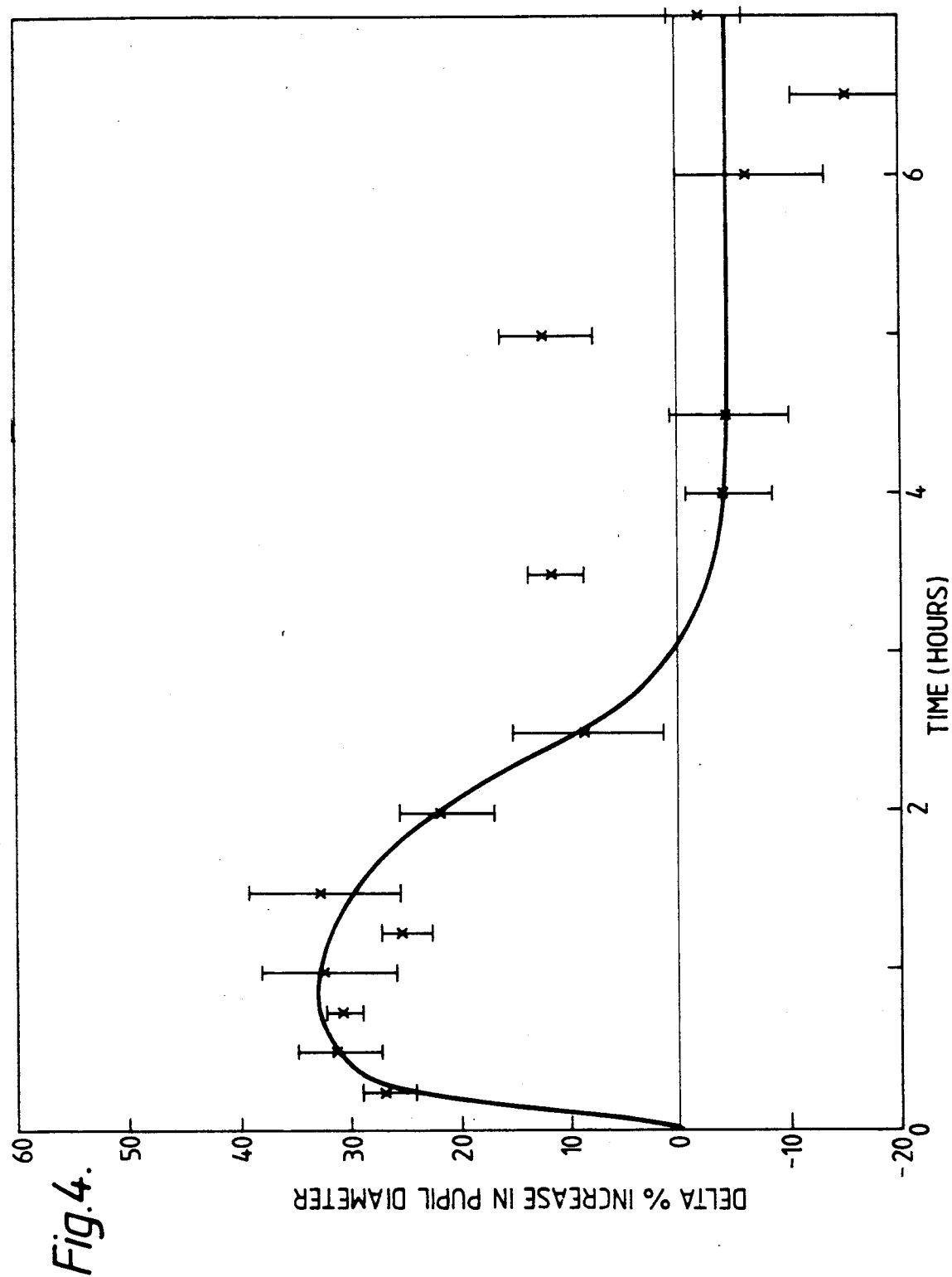
FIGS. 4 and 5 are graphical representations of mean differences (with standard error bars) in percentage change between the test and control eyes for indicated time points.

The mean differences (with standard error bars) in percentage change between the test and control eyes for each time point are depicted graphically in FIG. 4. This shows that there is significant magnitude and duration of mydriatic response to the ephedrine formulation when applied at considerably lower volume than with conventional methods of treatment.

EXAMPLE 2

The experimental procedure described in Example 1 was repeated, but administering to the eye 3.5 $\mu$l of a 4% w/w solution of pilocarpine in dimethylisosorbide:water (95:5 w/w) containing 3% of hydroxypropyl cellulose as a viscolizer, and measuring the miotic effect produced.

The miotic response of the treated eye to pilocarpine at each time point was calculated as follows:

% decrease in pupil diameter at time $t =$

-continued
$$\frac{T_o - T_t}{T_o} - \frac{C_o - C_T}{C_o} \times 100$$

where $T_o$ and $C_o$ are the pretreatment pupil diameters of the test and control eyes respectively, and $T_t$ and $C_t$ are the pupil diameters of the test and control eyes respectively at time t.

Figure 5:
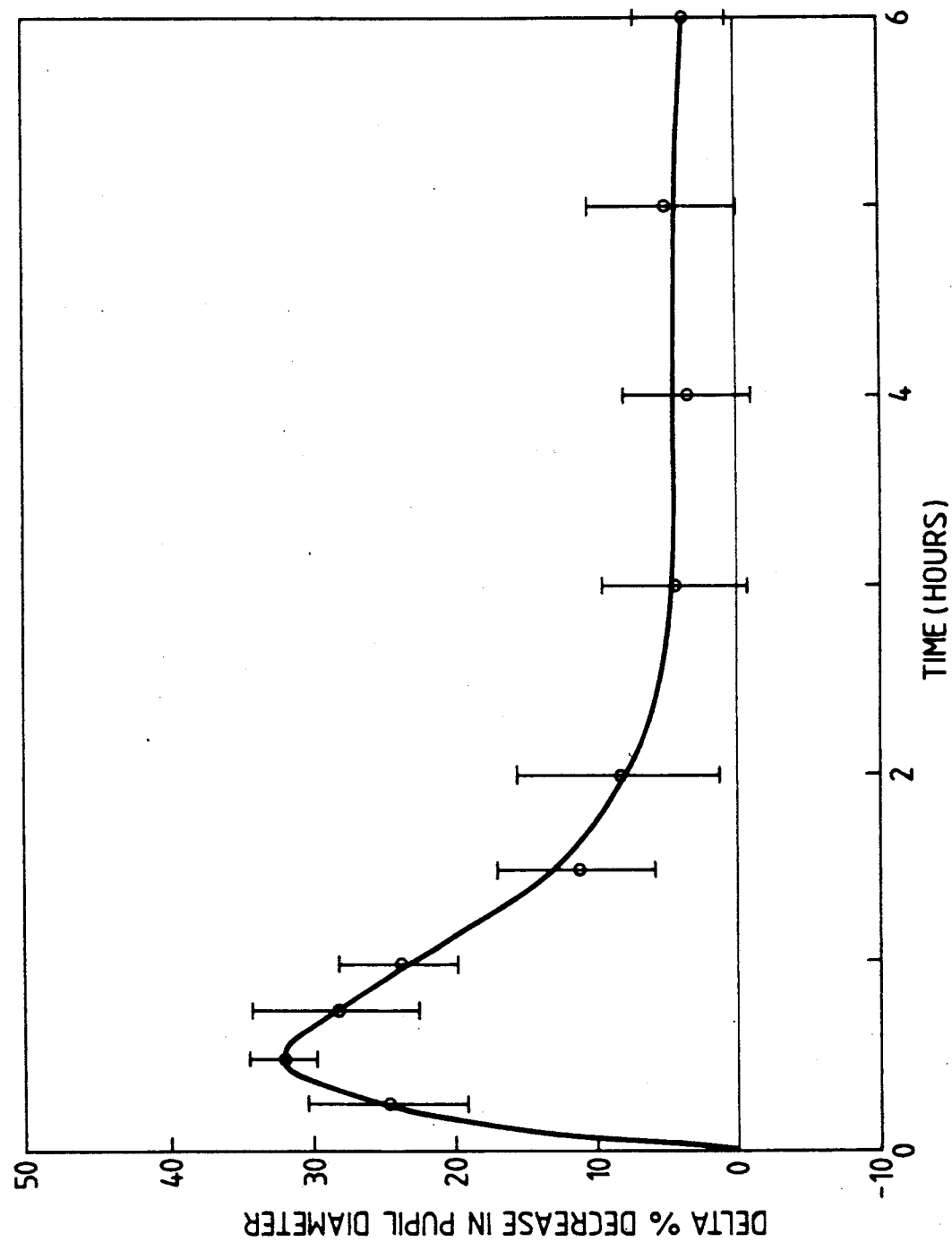

The mean differences (with standard error bars) in percentage change between the test and control eyes at each time point are depicted graphically in FIG. 5. This shows that there is significant magnitude and duration of miotic response to pilocarpine formulation when applied at considerably lower volume than with conventional methods of treatment.

What we claim is:

1. Electrodynamic spraying apparatus for dispensing a measured unit does of an opthalmically active liquid formulation for application to the corneal surface of an eye, said apparatus comprising:
    a housing;
    at least one spray nozzle attached to said housing having a liquid outlet of sufficiently small interior cross section to retain therein a measured unit does of formulation;
    means within said housing for supplying said measured unit dose of formulation to said nozzle outlet;
    means within said housing for causing said formulation to flow from said nozzle through said outlet;
    at least one electrode adjacent said nozzle outlet, which electrode is spaced from said outlet and electrically insulated from said nozzle; and
    means for applying an electrical potential difference between said spray nozzle outlet and said electrode of sufficient magnitude to draw said formulation from said outlet, and to atomize said formulation into a spray of electrically charged droplets;
    said apparatus being adapted, when said nozzle outlet is in a spaced relationship with said corneal surface, to cause said measured unit dose of formulation to be drawn to said corneal surface in the form of electrically charged droplets and uniformly deposited thereon.

2. Apparatus as claimed in claim 1 wherein the means for supplying the measured dose of the formulation to the nozzle is a metered valve.

3. Apparatus as claimed in claim 1 wherein the means for supplying the measured dose of the formulation to said nozzle is a syringe-pump.

4. Apparatus as claimed in claim 1 which is capable of electrically charging the spray nozzle to potential of between 1 to 20 kV relative to said electrode.

5. The apparatus as claimed in claim 1 additionally including a receiving member for demountably attaching said nozzle, said nozzle being replaceable and adapted to contain a single measured unit dose of said formulation.

6. Apparatus as claimed in claim 5 wherein said means for causing said formulation to flow from said nozzle through said outlet being such that it simultaneously activates the high voltage generator.

7. Apparatus as claimed in claim 1 wherein said means for applying an electrical potential difference between said spray nozzle outlet and said electrode is a high voltage generator.

8. Apparatus as claimed in claim 7 wherein said high voltage generator is powered by batteries.

9. Apparatus as claimed in claim 8 wherein said batteries for the high voltage generator are located in the apparatus, which is suitably dimensioned for hand-held usage.

* * * * *